United States Patent [19]

Koch et al.

[11] Patent Number: 4,492,524
[45] Date of Patent: Jan. 8, 1985

[54] MULTIPLE PISTON PUMP WITH A CONSTANT DISCHARGE CAPACITY

[75] Inventors: Dieter Koch, Ettlingen; Tonio Gianotti, Weinheim, both of Fed. Rep. of Germany

[73] Assignee: Bruker-Analytische Messtechnik GmbH, Rheinstetten-Forchheim, Fed. Rep. of Germany

[21] Appl. No.: 303,057

[22] Filed: Sep. 17, 1981

[30] Foreign Application Priority Data

Sep. 23, 1980 [DE] Fed. Rep. of Germany ....... 3035770

[51] Int. Cl.³ .................. F04B 49/06; F04B 49/08
[52] U.S. Cl. .................. 417/18; 417/273; 210/101
[58] Field of Search ........ 417/22, 42, 18, 29, 417/273, 521; 92/133; 210/101

[56] References Cited

U.S. PATENT DOCUMENTS

| | | | |
|---|---|---|---|
| 3,847,507 | 11/1974 | Sakiyama | 417/42 |
| 3,882,861 | 5/1975 | Kettering | 417/44 |
| 4,028,018 | 6/1977 | Audsley | 92/13.3 |
| 4,173,437 | 11/1979 | Leka | 417/521 |
| 4,180,375 | 12/1979 | Magnusson | 417/22 |
| 4,233,156 | 11/1980 | Tsukada | 210/101 |
| 4,255,088 | 3/1981 | Newton | 417/1 |
| 4,299,541 | 11/1981 | Ohara | 417/44 |
| 4,321,014 | 3/1982 | Eburn | 417/29 |
| 4,326,837 | 4/1982 | Gilson | 417/22 |
| 4,352,636 | 10/1982 | Patterson | 417/22 |
| 4,359,312 | 11/1982 | Funke | 417/18 |

*Primary Examiner*—William L. Freeh
*Attorney, Agent, or Firm*—Burmeister, York, Palmatier, Hamby & Jones

[57] ABSTRACT

A multiple piston pump with a constant discharge capacity for liquid chromatographs comprises at least three piston-cylinder units (1,2,3), whereof the pistons (7) are driven through a non-linear drive by a motor (23) with a mutual phase displacement of 360°/n, when n represents the number of piston-cylinder units. A regulating system varies the speed of the motor (23) during each period or cycle of the piston movement in such a manner as to compensate for the non-linear drive so that the pressure of the liquid conveyed during each period or cycle remains at least approximately constant. The motor (23) can be constructed as a stepping motor, which is supplied with current pulses whereof the frequency determines the speed of the motor.

19 Claims, 4 Drawing Figures

MULTIPLE PISTON PUMP WITH A CONSTANT DISCHARGE CAPACITY

FIELD OF THE INVENTION

The invention relates to a multiple pump with a constant discharge capacity for liquid chromatographs, whereof the drive comprises a motor and a regulating system responding to the pressure of the liquid conveyed for changing the speed of the motor and consequently the discharge capacity depending on the liquid pressure.

BACKGROUND OF THE INVENTION

For liquid chromatography, it is necessary to produce a liquid stream which flows through the chromatographic column at high pressure with the greatest possible continuity. The pressures to be employed in this case are in the order of magnitude of several hundred Bars with a discharge capacity of up to 10 ml/min. With a pressure in the order of magnitude of several hundred Bars, an appreciable compression of the liquid occurs.

German OS No. 23 11 016 discloses a multiple piston pump of the aforementioned type, which comprises two piston-cylinder units, which are driven by a motor with the interposition of a transmission comprising gears constructed in an elliptical manner and arranged eccentrically so that the sum of the respective piston displacements of both cylinders in the compression direction is equal to a constant, so that the piston pump has a constant discharge capacity on account of its mechanical construction. The regulating system responding to the pressure of the liquid conveyed serves to vary the speed of the motor in the case of a charge in the pressure so that variations in the rate of delivery caused by the compression of the liquid are compensated for and the rate of delivery remains constant even with changes of pressure.

As mentioned, in the known piston pump, the constant discharge capacity depends on its mechanical construction. This construction must be carried out with extremely high accuracy, in order to ensure a constant discharge capacity in the case of small discharge capacities. Furthermore, the manufacture and assembly of elliptical and eccentric gears involves considerable difficulties.

SUMMARY OF THE INVENTION

In contrast thereto, it is the object of the invention to provide a multiple piston pump with a constant discharge capacity, which has a significantly simplified mechanical construction and in particular requires no transmission with elliptical and eccentric gears.

This object is achieved according to the invention due to the fact that the piston pump comprises at least three piston-cylinder units, whereof the pistons are driven through a non-linear drive by the motor with a mutual phase displacement of 360°/n, when n represents the number of piston-cylinder units and the regulating system is designed for the variation of the speed of the motor during each period or cycle of the piston movement to compensate for the non-linear drive so that the pressure of the liquid conveyed remains at least approximately constant during each period or cycle.

Thus, in a manner other than in the known piston pump, a constant discharge capacity is achieved in this case not on account of the mechanical construction, but by regulating the speed of the drive motor for the piston pump. When using three piston-cylinder units, which are operated by a simple non-linear eccentric drive with a phase displacement of 360°/3=120° with respect to each other, the liquid streams conveyed by the three piston-cylinder units add up to a total stream whereof the fluctuations without additional measures amount to approximately 13%. In a liquid analytical instrument, since one works against a high flow resistance, which necessitates the high discharge pressure, these fluctuations of the discharge capacity are expressed as a corresponding fluctuation in the pressure of the liquid conveyed, which is utilized according to the invention for varying the speed of the motor during each period or cycle of the piston movement so that the fluctuations in the discharge capacity, which would occur with a constant speed of the motor due to the non-linear eccentric drive, are compensated for. Accordingly, the invention makes it possible whilst using simple regulating operations to provide a multiple piston pump with a constant discharge capacity, without necessitating complicated and expensive mechanical measures.

It will be understood that a multiple piston pump according to the invention could also be constructed with more than three piston-cylinder units. However, since due to the use of additional piston-cylinder units, the construction of a control loop is not appreciably influenced and each additional piston-cylinder unit involves expenditure, at present a pump with three piston-cylinder units is regarded as optimum.

As aforementioned, with the multiple piston pump according to the invention, a speed regulation of the motor takes place in such a manner that the pressure of the liquid conveyed remains constant. However, the pressure of the liquid conveyed depends not only on the discharge capacity, but also on the viscosity of the liquid conveyed. If the viscosity of the liquid conveyed increases, then with a constant discharge capacity, the pressure in the liquid conveyed increases. Accordingly, when the pressure is kept constant, any change in the viscosity of the liquid conveyed results in a change in the discharge capacity. However, in liquid chromatography, one frequently works with solvent mixtures, whose composition is changed within the course of an analysis, so that the viscosity of the liquid conveyed also changes in the course of an analysis. In order to keep the discharge capacity also constant in this case, it is provided in a further embodiment of the invention that the regulating system comprises a device which is not pressure-dependent for monitoring the mean speed of the motor and for keeping it constant. Since in piston pumps, the speed of the motor is a direct measurement of the discharge capacity, the discharge capacity also remains constant if the mean speed is kept constant. Then, the sole purpose of the pressure-dependent regulation is to determine the variation of the speed of the motor, which is identified when monitoring the mean speed.

As above mentioned, to a certain extent the discharge capacity depends on the compression which the liquid experiences with the prevailing discharge pressure. Therefore, also in the piston pump according to the invention, the regulating system may comprise a device for varying the speed of the motor depending on the mean pressure of the liquid conveyed so that the delivery rate remains constant due to compensation of the pressure-dependent compression of the liquid.

This device for varying the speed can basically be constructed as described in the above mentioned German OS No. 23 11 016. However, it is more advantageous if the device for varying the speed comprises a sensor responding to the pressure prevailing within at least one of the piston-cylinder units and varies the speed of the motor depending on the distance covered by the piston from its bottom dead centre until the build-up of the operating pressure. The pressure in the piston-cylinder unit must build-up from the pressure of the flowing medium to the discharge pressure and then remain constant until the end of the compression stroke. The transition from the pressure rise to constant pressure can be monitored by measuring techniques so that in this way the travel of the piston until the build-up of the operating pressure can be ascertained and depending thereon the discharge capacity of the pump can be compensated, without data relating to the compressibility of various liquids having to be available as a function of the operating pressure.

In a preferred embodiment of the invention, the motor for driving the piston pump is constructed as a stepping motor, which is supplied with current pulses whereof the frequency determines the speed of the motor. The regulating system is then constructed in order to influence the frequency of the current pulses. In stepping motors, one revolution of the motor is divided into a very large number of steps, so that due to the variation of the pulse frequency and thus of the chronological sequence of the individual steps, a very fine regulation of the speed of the motor is possible during each period of the piston movement. Influencing the frequency of the current pulses is then particularly simple if the current pulses for the motor are produced by a driver responding to control pulses and a pulse source is available which supplies control pulses at a frequency which is higher than the frequency which corresponds to the reference speed of the motor and provided between the pulse source and the driver is a controllable frequency divider to which a pressure-dependent control signal is supplied, which adjusts the divider ratio of the frequency divider to values such that the control pulses supplied to the driver have frequencies which are alternately higher and lower than the frequency corresponding to the reference speed. It will be understood that these frequency variations can be random and of different magnitude and can also vary as regards time. In a preferred embodiment of the invention, the frequency corresponding to the reference speed amounts to two thirds the frequency of the control pulses supplied by the pulse source and the frequency divider can be set to the divider ratios 1:1 and 1:2. A regulating system operating under such conditions can be produced at extremely low cost.

With a direct supply of the control pulses supplied by the frequency divider to the driver, the frequency of the current pulses supplied by the driver and consequently the rotary ratio of the stepping motor would fluctuate in the ratio 1:2. Smoothing of these fluctuations can be achieved due to the fact that connected between the controllable frequency divider and the driver is a further frequency divider with a fixed reduction ratio. In practice, an additional frequency divider with the divider ration of 1:8 has proved particularly suitable. It will be understood that when using an additional frequency divider of this type, the frequencies of the control pulses must be selected higher by the divider ratio of this frequency divider than would be necessary if the control pulses were supplied directly by the frequency divider to the driver.

In a preferred embodiment of the invention, the regulating system comprises an electrical pressure convertor responding to the pressure of the liquid conveyed, the output signal of which convertor is supplied by way of a high-pass filter and an adding stage, in which the output signal is superimposed on a reference direct voltage, to a threshold value discriminator, whereof the output signal controls the adjustment of the frequency divider. In this case, the reference direct voltage determines the mean speed of the motor, whereas owing to the use of a high-pass filter, only those components of the signal, which the electrical pressure convertor supplies, are taken into consideration, which can be traced back to rapid pressure fluctuations and therefore serve for the variation of the speed of the motor during each period of the piston movement. This arrangement has the particular advantage that the reference direct voltage may be a control voltage derived from the speed of the motor. In a particularly simple manner, this control voltage may be characteristic of the difference between the frequency corresponding to the reference speed and the mean frequency of the control pulses supplied to the driver and may bring about a reduction of this difference.

In order to form this control voltage, in a particularly simple manner, a first pulse signal characteristic of the frequency corresponding to the reference speed can be supplied to one input and a second pulse signal characteristic of the instantaneous frequency of the control pulses supplied to the driver can be supplied to the outer input of a forwards-backwards counter, so that the counting state is always equal to the difference between the pulses supplied by both pulse signals. The control voltage used as the reference direct voltage may then be an analog voltage derived from the respective counting state.

If, as mentioned above, the frequency corresponding to the reference speed amounts to two thirds of the frequency of the control pulses supplied by the pulse source and the freqency divider can be set to the divider ratios 1:1 and 1:2, then advantageously the first pulse signal can be formed by a uniform pulse sequence, whereof the frequency is equal to one third of the frequency of the control pulses supplied by the pulse source and when set to the divider ratio 1:2, the frequency divider supplies every other control pulse to the counter as a second pulse signal, instead of to the driver.

The above mentioned device for varying the speed depending on the pressure of the medium, which serves to equalize the compression of the liquid, can in a particularly simple manner bring about a pressure-dependent variation of the frequency of the control pulses supplied by the pulse source.

BRIEF DESCRIPTION OF THE DRAWINGS

Further details and embodiments of the invention will become apparent from the following description of the embodiment illustrated in the drawings. The features revealed by the description and drawings can be used in other embodiments of the invention individually or jointly in any combination.

DETAILED DESCRIPTION OF ILLUSTRATIVE EMBODIMENTS

Figure 1:
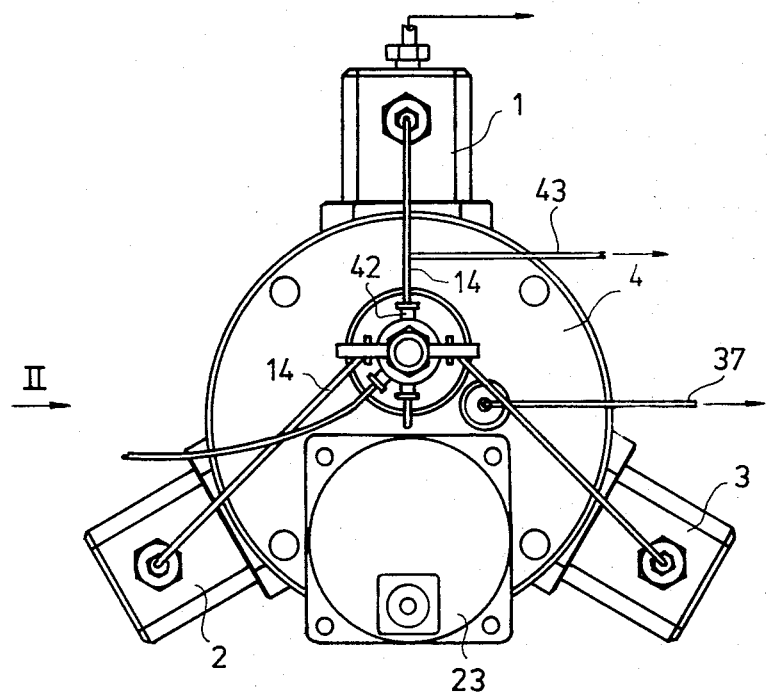
FIG. 1 is a view of a multiple piston pump according to the invention.
Figure 2:
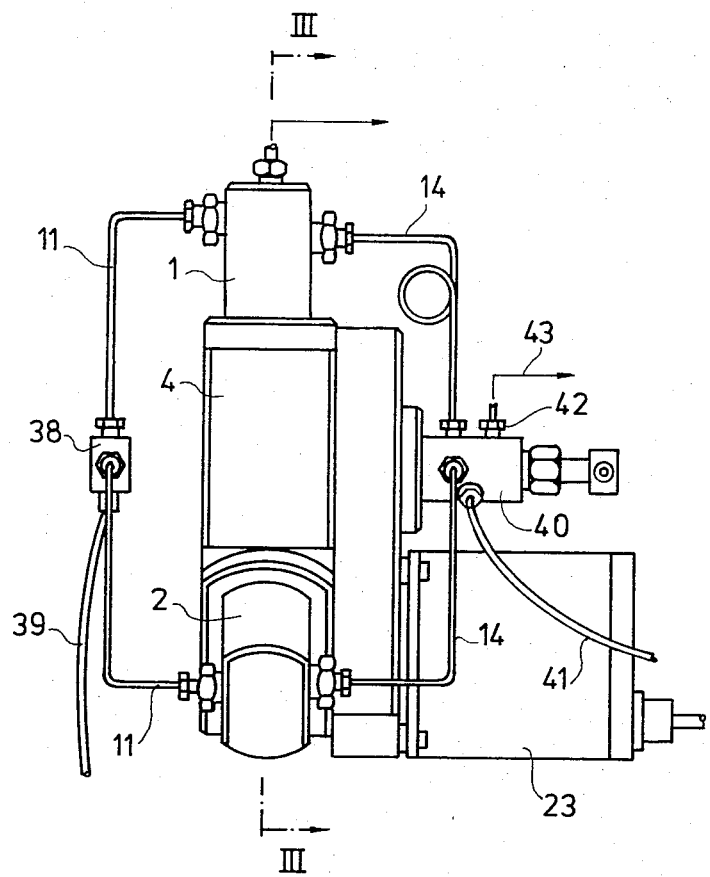
FIG. 2 is a view of the pump according to FIG. 1 in the direction of arrow II.
Figure 3:
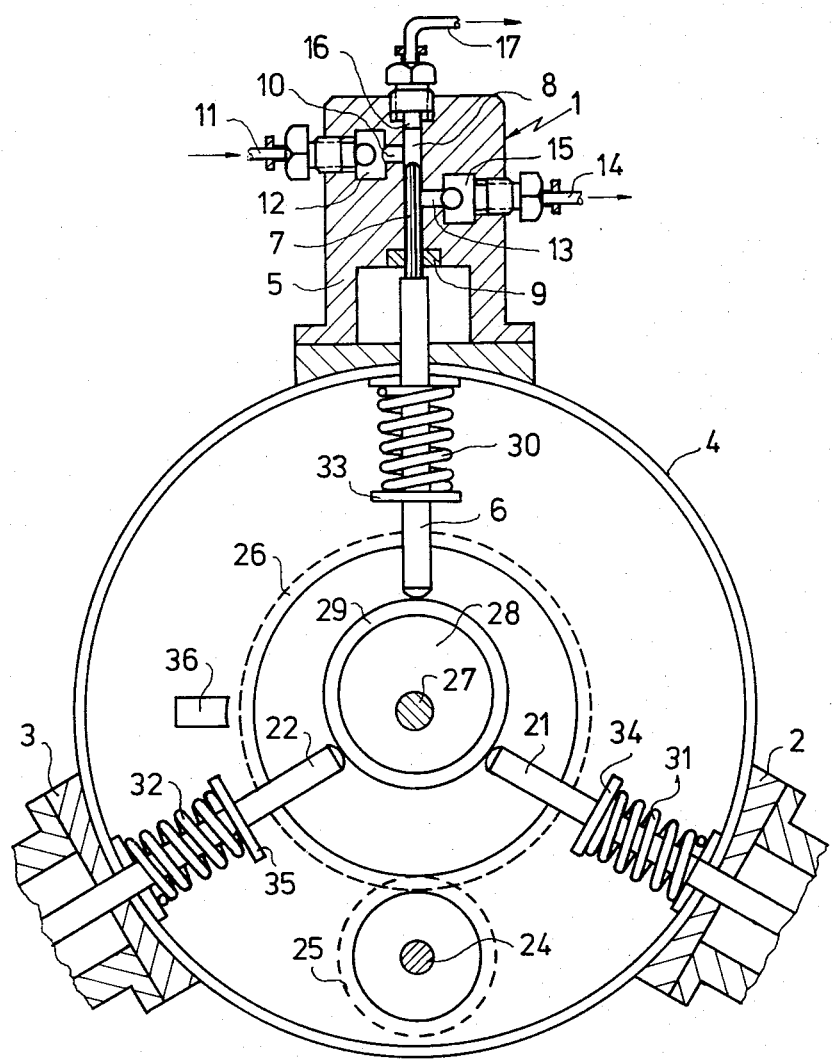
FIG. 3 is a diagrammatic section on line III—III through the pump according to FIG. 2

The piston pump illustrated in FIGS. 1 to 3 comprises three piston-cylinder units 1 to 3, which are flange-mounted on the surface of a cylindrical casing. The three piston-cylinder units 1 to 3 have the same construction and consist respectively, as shown in detail in FIG. 3 for the piston-cylinder unit 1, of a cylinder block 5 and a plunger 6, whereof the front end of reduced diameter forms the piston 7. The piston 7 projects into a thin cylinder bore 8 of the cylinder block 5 and is sealed at its rear end with respect to the cylinder block by a seal 9 shown only diagrammatically. Opening into the cylinder bore 8 is a radial bore 10, to which an inlet pipe 11 is connected. Located between the inlet pipe 11 and the radial bore 10 is a non-return valve 12, which blocks the feed pipe 11 during the delivery stroke of the piston. The pipe 14 containing the medium conveyed is connected to a second radial bore 13. In this case also, a non-return valve 15 is located between the radial bore 13 and the outlet pipe 14, which non-return valve blocks the pipe 14 during the suction stroke of the pump. Located at the end of the cylinder bore 8 is a sensor 16, which produces an electrical signal proportional to the pressure prevailing in the cylinder and supplies it on a lead 17 to the microprocessor 18 of the regulating system (FIG. 4).

Serving to drive the plunger 6 of the piston-cylinder unit 1 as well as the plungers 21 and 22 of the piston-cylinder units 2 and 3 is a stepping motor 23, which is fastened to an end wall of the casing 4. Its drive shaft 24 projects into the casing 4 and supports a gear 25, which meshes with a gear 26 of larger diameter mounted in the casing 4. Mounted eccentrically on the same shaft 27 as this gear 26 is a cam disc 28, on the periphery of which the plungers 6, 21 and 22 are seated by their ends. In order to reduce the friction, a ring 29 mounted to rotate on the periphery of the cam disc 28 can be provided between the cam disc 28 and the ends of the plungers 6,21 and 22. The plungers 6,21 and 22 are respectively acted upon by a compression spring 30,31,32 which is supported at one end against the surface of the casing 4 and at the other end against a flange or collar 33, 34,35 located on the plunger. Since the three plungers 6,21 and 22 are off set at an angle of 120° with respect to each other, radially with respect to the shaft 27 supporting the cam disc 28 and cooperate with the same cam disc 28, they carry out their movements controlled by the cam disc 28, with a phase displacement of 120° with respect to each other. Furthermore, with this arrangement, the position of the pistons is a direct function of the position of the gear 26 driving the cam disc 28. Consequently, the teeth of the gear can be utilized at the same time as a digital transmitter for ascertaining its angular position and thus for determining the piston positions. The teeth can be scanned by suitable optical or electrical means, for example by means of an inductive tracer 36, as shown diagrammatically in FIG. 3. The signals produced by the tracer 36 are supplied by means of a lead 37 leaving the casing 4 likewise to the microprocessor 18 (FIG. 4). The supply pipes 11 of the three cylinder-piston units 1 to 3 lead to a distributor 38, from which a pipe 39 leads to the medium to be conveyed. In a similar manner, the outlet pipes 14 are connected to a distributor 40, from which a common high pressure pipe 41 leads to the column of a liquid chromatograph. Also connected to this distributor 40 is a pressure convertor 42, whereof the signal characteristic of the pressure prevailing is supplied by way of a lead 43 to a high-pass filter 44 of the regulating system. Like the sensor 16, the pressure convertor 42 may also be a piezo-electric component. However, unlike the sensor 16, which sends a signal which is characteristic of the changing pressure in an individual cylinder, the pressure convertor 42 sends a signal which is characteristic of the pressure in the entire stream, which is formed from the addition of the streams conveyed by the three piston-cylinder units in the distributor 40. This pressure is substantially proportional to the instantaneous total discharge rate of the liquid, which is supplied to the chromatographic column of the analytical instrument having a very high flow resistance. When superimposing the quantities of liquid which are supplied by three piston-cylinder units operating with a phase displacement of 120° with respect to each other, a stream is produced in which the discharge capacity fluctuates by approximately 13%. With the pump according to the invention, this fluctuation is equalized by means of a regulating system, which responds to the pressure fluctuations resulting from the fluctuations of the discharge capacity and accordingly varies the speed of the stepping motor during each period of the piston movement.

The speed of the stepping motor 23 is determined by the frequency of the current pulses, with which it is supplied, because the rotor of the stepping motor is rotated by each current pulse stepwise by a certain angular amount. For example, one revolution of the motor can be divided into 500 steps.

Figure 4:
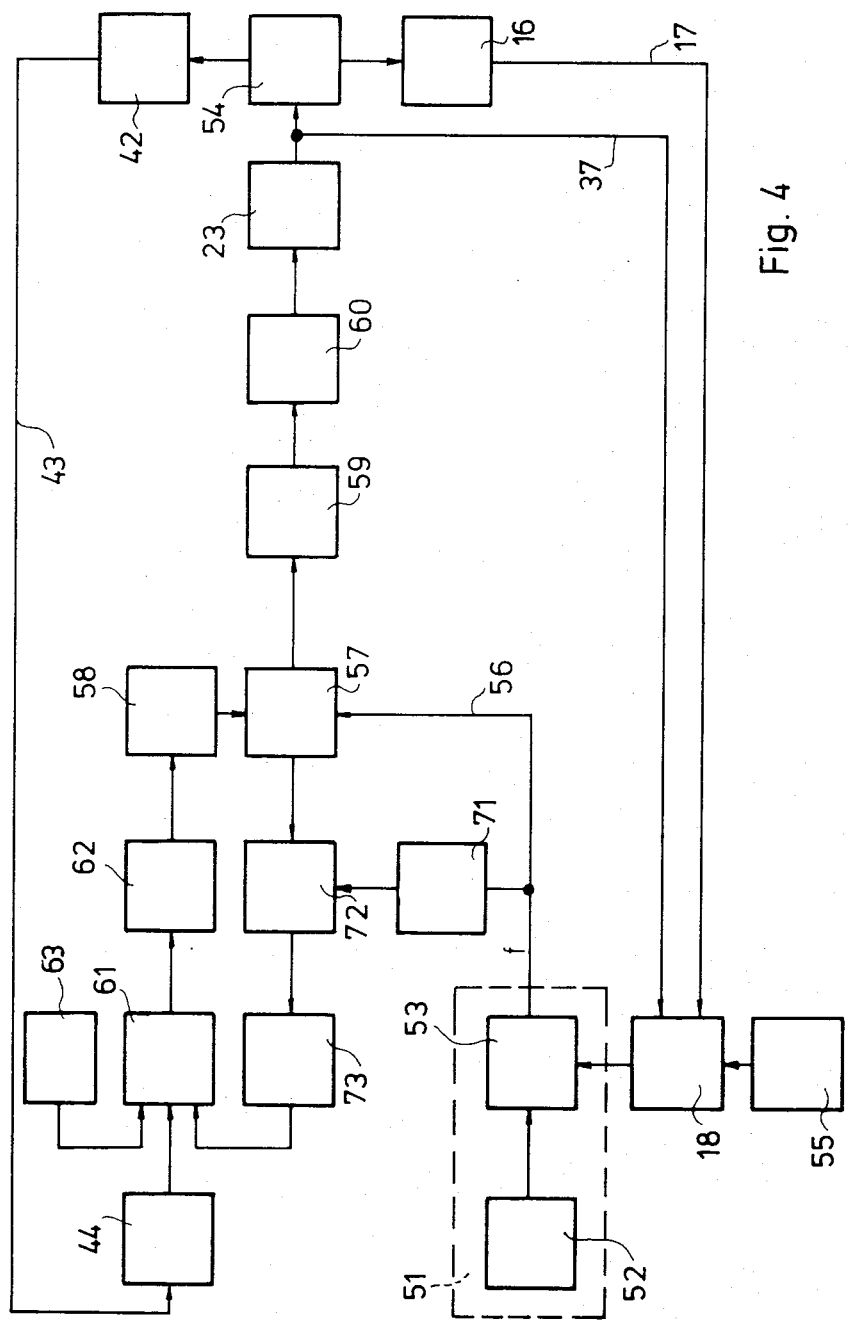
FIG. 4 is the block circuit diagram of the regulating system of the pump illustrated as an embodiment.

In the embodiment illustrated by the block circuit diagram according to FIG. 4, the current pulses required for operating the stepping motor are produced by a driver 60, which responds to control pulses and in addition to the necessary power amplifiers comprises a de-coder or fixed store (not shown in detail), which upon the arrival of a control pulse, respectively initiates a set of for example five phase-shifted current pulses necessary for driving the stepping motor. The control pulses are supplied by a pulse source 51, which comprises an oscillator 25 and a divider 53, whereof the divider ratio 1:n can be varied in small steps. The divider ratio is determined by the output signal of a microprocessor 18, into which a desired speed of the stepping motor 23 or a desired discharge capacity of the pump 54, which is illustrated in the block circuit diagram according to FIG. 4 by the box 54, can be fed by means of an adjustor 55. Then, with the assistance of stored data, the microprocessor determines the divider ratio 1:n of the divider 53, which in turn determines the frequency of the control pulses, which are supplied to the driver 60.

The control pulses of frequency f supplied accordingly by the pulse source 51 are supplied on the lead 56 to a divider 57, which can be adjusted by means of a switching member 58 to the reduction ratios 1:1 and 1:2. The output signal of the divider 57 is supplied to a further divider 59, which reduces the frequency of the control pulses once more in the ratio 1:8, before they are supplied to the driver 60, which supplies the stepping motor 23.

The frequency f of the control pulses supplied by the pulse source 51 is chosen so that the stepping motor 23 would operate at the desired speed and the pump 54 would have the desired discharge capacity, if the frequency of the control pulses amounted to 2f/3. Therefore, the stepping motor 23 operates too quickly, if the divider 57 does not reduce the frequency f of the control pulses (divider ratio 1:1) and too slowly, if the divider 57 supplies the control pulses at the frequency f/2. Consequently, a pressure rise or a pressure drop occurs in the liquid conveyed by the pump 54, to which the pressure convertor 42 responds and supplies an electrical signal, which is supplied via the lead 43 to the high-pass filter 44. The result of using the high-pass filter 44 is that the output signal of the high-pass is characteristic solely of the fluctuations of the pressure over a period of time and comprises no components characteristic of the mean pressure. Therefore, the output signal of the high-pass filter can be superimposed in a subsequent adding or summing stage 61 on a reference direct voltage, which is coordinated with the response threshold of a Schmitt trigger or bistable threshold value discriminator 62 so that the Schmitt trigger is tripped in the range of positive sections of the signal supplied by the high-pass filter. During the period of time for which the control signal supplied by the high-pass filter 44 trips the Schmitt trigger 62, the output signal of the electronic switching member or stage 58 causes a change-over of the divider 57 to the ratio 1:2, so that the speed of the stepping motor 23 and accordingly also the discharge capacity of the pump 54 is reduced. The pump operates at a reduced discharge capacity until the signal supplied by the pressure convertor 42 once more falls below the threshold value of the Schmitt trigger, whereupon the output signal of the Schmitt trigger 62 changes in a corresponding manner and causes the switching member 58 to restore the divider 57 to the ratio 1:1. After this, the stepping motor 23 again operates at increased speed, so that the discharge capacity of the pump 54 and accordingly also the pressure in the liquid conveyed once more rises until on exceeding the threshold value of the Schmitt trigger 62, the divider 57 again switches back.

The control loop described has a very simple construction, because it is only necesssary for a divider to be changed from the divider ratio 1:1 to the divider ratio 1:2. In the simplest manner, an arrangement of this type may be provided in that in the divider, every other pulse of the control pulses is suppressed. Above all, due to the use of a divider of this type, the speed jumps are very considerable. However, the use of the additional divider 1:8 brings about averaging, in particular if a change of the reduction ratio occurs frequently, so that the actual speed variations do not take place in the ratio 1:2 or 2:1, but in the ratio $(8+k_1):(8+k_2)$, if $k_1$ and $k_2$ respectively represent a whole number from 0 to 8, which indicates how many of the control pulses of frequency f have been suppressed by the divider 57 in successive counting intervals of the divider 59 as a result of switching-over to the divider ratio 1:2.

When a reference direct voltage is supplied to the adding stage 61 solely by a voltage source 63, the reference voltage represents a predetermined-mean pressure in the liquid conveyed by the pump 54. Maintaining such a pressure can be advisable as long as the liquid to be conveyed has a constant viscosity. However, if the viscosity of the liquid conveyed varies as a result of long term temperature changes or, however, as a result of a change in the composition of the liquid conveyed, then a change in the delivery pressure is related to this change of viscosity, when the discharge capacity is constant. With a constant discharge capacity, an increase in the viscosity also results in an increase in the pressure and vice versa. However, if therefore the pressure is kept constant despite such changes of viscosity, this can only take place due to a corresponding change in the discharge capacity, which however is undesirable. Therefore, the regulating system illustrated in FIG. 4 also comprises members for keeping the discharge capacity constant. These members comprise a frequency divider 71 connected to the pulse source 51, which divider reduces the control pulses with the frequency f by the ratio 1:3 and a fowards-backwards or up-down counter 72, to which the output signal of the divider 71 is supplied as a first pulse signal and as a second pulse signal, those pulses are supplied by the divider 57, which are suppressed when this divider is adjusted to the divider ratio 1:2. The output signal of the 1:3-divider is supplied to the backwards or down counting input and the output signal of the 1:2-divider 57 is supplied to the forwards or up counting input of the counter 72. When the stepping motor 23 operates at the desired speed, the mean frequency of the control pulses supplied by the divider 57 must amount to 2f/3. This is the case when on average, each third pulse of the control pulses with the frequency f is suppressed by the divider 57, so that these suppressed pulses form a pulse train with the mean frequency f/3. The second pulse signal accordingly likewise has the frequency f/3 and the counter 72 stops at a predetermined state, when the divider 57 supplies control pulses to the driver 60, the frequency of which leads to the desired speed of the stepping motor. On the other hand, if the control pulses supplied by the divider 57 vary in their mean frequency from the value 2f/3 and consequently the second pulse signal varies from the mean frequency f/3, because the pressure convertor 42 announces a pressure change in the same direction, then the digital state or count of the counter 72 is changed. A direct analog voltage is derived from the digital state or count of the counter 72 by means of a digital to analog convertor 73, which direct voltage is supplied to the adding or summing stage 61 and which brings about such a shift of the signal supplied by the high-pass filter 44, with respect to the threshold of the Schmitt trigger 62 that the deviation from the reference value recorded by the counter 72 is reduced. In this way it is possible by means of the control loop containing the pressure convertor 42 to compensate for the rapid pressure fluctuations in the liquid stream conveyed and thus for the momentary fluctuations in the discharge capacity and thus at the same time to keep the average speed of the stepping motor 23 and thus the average discharge capacity of the pump 54 constant, irrespective of long term pressure fluctuations, such as may be caused in particular by changes in viscosity.

Exact proportionality between the speed of the stepping motor 23 and the discharge capacity of the pump 54 exists only as long as the liquid conveyed can be regarded as noncompressible. However, feed pumps for chromatographic analytical instruments operate at pressures which can amount to 300 Bars and above. At such pressures, liquids are already more or less compressible, so that strict proportionality between the speed of the stepping motor 23 and the discharge capacity of the pump 54 no longer exists. In order to ensure that the desired discharge capacity is achieved, despite compression of the liquid conveyed, the pressure prevailing in the pump cylinder is measured by means of the sensor 16. This pressure increases from the pressure or the fluid sucked in, i,e. generally from atmospheric pressure, at the beginning of the delivery stroke up to the pressure prevailing in the liquid conveyed, before the liquid can be ejected from the cylinder by overcoming the nonreturn valve located before the outlet pipe. When the discharge pressure is reached, the pressure in the cylinder remains constant. The output signal of the sensor 16 is supplied to a micro-processor 18, which responds to the instant at which the pressure passes from the increasing part into the constant part and by means of the signal supplied by the sensor 36 on the lead 37 ascertains how great the stroke of the piston was until the delivery pressure was reached.

On the basis of this data, the micro-processor 18 brings about a change in the divider ratio n of the divider 53, in order to increase the frequency f of the control pulses supplied by the pulse source 51 by so much that the delivery volume reduced as a result of the compression is compensated for by an increase in the speed of the stepping motor 23.

It will be understood that the invention is not restricted to the embodiment illustrated, but that variations thereof are possible without diverging from the scope of the invention. Such variations may relate both to the mechanical construction of the pump, in particular to the number of cylinders used, although an increase in the number of cylinders does not seem appropriate, on the one hand because each additional cylinder represents increased mechanical expenditure, which has no effect on the construction of the regulating system and on the other hand, an increase in the number of cylinders must result either in a reduction of the stroke volume per cylinder and/or a reduction of the motor speed, if the same discharge capacity is to be achieved. However, both seem unfavourable. Likewise, it will be understood that the regulating system itself can be constructed in a different manner, for example due to the increased use of analog or digital components, and also for example due to the omission of the compensation of the liquid compression at high pressures. The micro-processor 18 could also be completely dispensed with and the adjustor 55 could be connected directly to the 1:n-divider 53.

We claim:

1. A multiple piston pump with a constant discharge capacity for liquid chromotography,
said pump comprising at least three piston-cylinder units having their individual liquid discharge outlets connected to a common liquid discharge outlet,
a single electric stepping motor providing the motive power for operating all of said piston-cylinder units,
a single circular eccentric rotatable drive cam operable by said motor for operating all of said piston-cylinder units,
said circular eccentric rotatable drive cam having a rotary cycle in which said piston-cylinder units are operated in sequence with equal phase displacement intervals therebetween of 360° divided by the number of piston-cylinder units,
said circular eccentric drive cam affording a non-linear relationship between the rotary speed of said motor and the linear speed of each piston-cylinder unit during its pumping stroke,
a pressure transducer for producing an electrical signal corresponding to the pressure in said common discharge outlet,
said piston-cylinder units producing a combined liquid discharge tending to have pressure pulsations therein at said common liquid discharge outlet,
and an electronic control system connected between said pressure transducer and said stepping motor for regulating the instantaneous speed of said motor to maintain at least approximately constant outlet discharge pressure and thereby to maintain at least approximately constant discharge capacity,
said electronic control system having fast response regulating means for rapidly changing the speed of said motor in response to outlet pressure pulsations during each cycle of said circular eccentric drive cam so as to minimize said pulsations and thereby compensate for the non-linear character of said drive cam so as to maintain the outlet pressure at least approximately constant during each cycle of said drive cam,
said fast response regulating means including a high-pass filter for receiving and passing the pulsations in the pressure signals from said pressure transducer while withholding any substantial transmission of long term changes in the pressure signals,
means for supplying a reference direct voltage,
a summing stage for receiving the pulsating signals from said high-pass filter and for superimposing said pulsating signals upon said reference direct voltage to produce combined output signals,
a threshold value discriminator connected to said summing stage for receiving said combined output signals,
pulse generating means connected to said stepping motor for producing pulses to operate said stepping motor at a speed corresponding to the frequency of said pulses,
said pulse generating means including switchable pulse frequency changing means for switching the pulse frequency between a higher value and a lower value,
and electronic switching means connected between said threshold value discriminator and said switchable means for switching the pulse frequency between its two values to speed up and slow down the instantaneous speed of said stepping motor to minimize such output pressure pulsations.

2. A multiple piston pump according to claim 1,
said pulse generating means comprising a pulse source,
said switchable means of said pulse generating means comprising a switchable frequency divider having its input connected to said pulse source and switchable between two different division ratios for producing said higher and said lower frequency output pulses to change the speed of said stepping motor.

3. A multiple piston pump according to claim 2,
including a speed monitoring device for monitoring the mean speed of the stepping motor,
and speed regulating means responsive to said speed monitoring device for changing the frequency of the pulses from said pulse source for keeping the mean speed of the motor constant.

4. A multiple piston pump according to claim 2,
including a speed monitoring device for monitoring the mean speed of the stepping motor, and speed regulating means responsive to said speed monitoring device for changing the frequency of the pulses produced by said pulse source for keeping the mean speed of the motor substantially constant, said speed regulating means comprising compressibility determining means for determining the compressibility of the liquid being pumped by said piston-cylinder units, and compressibility compensating means for increasing the frequency of the pulses produced by said pulse source to compensate for said compressibility.

5. A multiple piston pump according to claim 2, in which said higher and lower frequency pulses are at higher and lower frequencies than a reference frequency corresponding to an average reference speed of said stepping motor to maintain approximately the desired outlet pressure, said pulse source supplying pulses at a frequency f to said switchable frequency divider, said reference frequency corresponding to substantially two-thirds of the frequency f, said switchable frequency divider being switchable between division ratios of 1:1 and 1:2.

6. A multiple piston pump according to claim 2, including means for determining the compressibility of the liquid being pumped by the piston-cylinder units, and means for increasing the frequency of the pulses from said pulse source in proportion to such compressibility for correspondingly increasing the speed of the stepping motor and thereby compensating for such compressibility.

7. A multiple piston pump according to claim 5, said electronic control system comprising speed monitoring means for monitoring the speed of the stepping motor, and speed regulating means connected to said speed monitoring means and operable in response to variations in the mean speed of said motor for varying said reference direct voltage to keep said mean speed substantially constant.

8. A multiple piston pump according to claim 7, said speed regulating means comprising first means for deriving first frequency pulses from said pulse source and corresponding in frequency to said mean speed, second means for deriving second frequency pulses of a comparable frequency as a function of the frequency of the output pulses from said switchable frequency divider, difference means for deriving the difference between said first and second frequencies, and third means for producing a control voltage as a function of said difference and for employing said control voltage to vary said reference direct voltage in a direction to cause a reduction of said frequency difference.

9. A multiple piston pump according to claim 8, said difference means comprising an up-down counter having up and down counting inputs, said first means having its output connected to one of said counting inputs, said second means having its output connected to the other of said counting inputs, said up-down counter producing a digital count output corresponding to the difference between said first and second frequency, said third means comprising a digital to analog convertor for producing a control voltage corresponding to said digital count output, the output of said digital to analog convertor being connected to said summing stage to employ said control voltage to vary said reference direct voltage in such a direction as to reduce the difference between said first and second frequencies.

10. A multiple piston pump according to claim 9, said first means comprising a frequency divider having a division ratio of 1:3 to produce a first frequency which is one-third of the pulse frequency corresponding to said mean speed, said switchable frequency divider having its input receiving said pulse frequency corresponding to said mean speed, said switchable frequency divider being switchable between division ratios of 1:1 and 1:2 and being capable of maintaining a mean output pulse frequency which is two-thirds of its input pulse frequency, said switchable frequency divider being operative to suppress alternate pulses when switched to a division ratio of 1:2, said second means being operative to receive and utilize the suppressed pulses from said switchable frequency divider whereby said suppressed pulses are supplied as said second frequency pulses having a mean frequency which is one-third of the input pulses to the switchable frequency divider having a frequency corresponding to the mean speed of said motor.

11. A multiple piston pump with a constant discharge capacity for liquid chromotography, said pump comprising at least three piston-cylinder units having their individual liquid discharge outlets connected to a common liquid discharge outlet, a single electric stepping motor providing the motive power for operating all of said piston-cylinder units, a single circular eccentric rotatable drive cam operable by said motor for operating all of said piston-cylinder units, said circular eccentric rotatable drive cam having a rotary cycle in which said piston-cylinder units are operated in sequence with equal phase displacement intervals therebetween of 360° divided by the number of piston-cylinder units, said circular eccentric drive cam affording a non-linear relationship between the rotary speed of said motor and the linear speed of each piston-cylinder unit during its pumping stroke, a pressure transducer for producing an electrical signal corresponding to the pressure in said common discharge outlet, said piston-cylinder units producing a combined liquid discharge tending to have pressure pulsations therein at said common liquid discharge outlet, and an electronic control system connected between said pressure transducer and said stepping motor for regulating the instantaneous speed of said motor to maintain at least approximately constant outlet discharge pressure and thereby to maintain at least approximately constant discharge capacity, said electronic control system having fast response regulating means for rapidly changing the speed of said motor in response to outlet pressure pulsations during each cycle of said circular eccentric drive cam so as to minimize said pulsations and thereby compensate for the non-linear character of said drive cam so as to maintain the outlet pressure at least approximately constant during each cycle of said drive cam, said fast response regulating means including a high-pass filter for receiving and passing the pulsations in the pressure signals from said pressure transducer while withholding any substantial transmission of long term changes in the pressure signals, means for supplying a reference direct voltage, a summing stage for receiving the pulsating signals from said high-pass filter and for superimposing said pulsating signals upon said reference direct voltage to produce combined output signals, a threshhold value discriminator connected to said summing stage for receiving said combined output signals, an electronic driver connected to said stepping motor, pulse generating means connected to said driver of said stepping motor for producing motor control pulses to operate said stepping motor at a speed corresponding to the frequency of said pulses, said pulse generating means including switchable pulse frequency changing means for switching the motor control pulse frequency between a higher value and a lower value, electronic switching means connected between said threshhold value discriminator and said switchable means for switching the motor control pulse frequency between its two values to speed up and slow down the instantaneous speed of said stepping motor to minimize such output pressure pulsations, said pulse generating means comprising a pulse source for supplying source pulses of a frequency f, said switchable means of said pulse generating means comprising a switchable frequency divider having its input connected to said pulse source and switchable between two different division ratios for producing said higher and said lower frequency output pulses to change the speed of said stepping motor, said switchable frequency divider being switchable between division ratios of 1:1 and 1:2, and speed regulating means comprising first means for deriving first frequency pulses from said pulse source pulses and related in frequency to a mean speed to be established for the motor, second means for deriving second frequency pulses of a second frequency comparable with said first frequency as a function of the frequency of the output motor control pulses from said switchable frequency divider, difference means for deriving the difference between said first and second frequencies, and third means for producing a control voltage as a function of said difference and for employing said control voltage to vary said reference direct voltage in a direction to cause a reduction of said frequency difference, whereby the average frequency of said motor control pulses is regulated to correspond with said mean frequency.

12. A multiple piston pump according to claim 11,
said difference means comprising an up-down counter having up and down counting inputs, said first means having its output connected to one of said counting inputs, said second means having its output connected to the other of said counting inputs, said up-down counter producing a digital count output corresponding to the difference between said first and second frequency, said third means comprising a digital to analog convertor for producing a control voltage corresponding to said digital count output, the output of said digital to analog convertor being connected to said summing stage to employ said control voltage to vary said reference direct voltage in such a direction as to reduce the difference between said first and second frequencies.

13. A multiple piston pump according to claim 12,
said first means comprising a frequency divider having a division ratio of 1:3 to produce a first frequency which is one-third of the source pulse frequency f, said switchable frequency divider being switchable between division ratios of 1:1 and 1:2 and being capable of maintaining a mean output pulse frequency which is two-thirds of the source pulse frequency f, said switchable frequency divider being operative to suppress alternate pulses when switched to a division ratio of 1:2, said second means being operative to receive and utilize the suppressed pulses from said switchable frequency divider whereby said suppressed pulses are supplied as said second frequency pulses to be stabilized at an average frequency which is one-third of the source pulse frequency f.

14. A multiple piston pump with a constant discharge capacity for liquid chromotography,
said pump comprising at least three piston-cylinder units having their individual liquid discharge outlets connected to a common liquid discharge outlet, a single electric stepping motor providing the motive power for operating all of said piston-cylinder units, a single circular eccentric rotatable drive cam operable by said motor for operating all of said piston-cylinder units, said circular eccentric rotatable drive cam having a rotary cycle in which said piston-cylinder units are operated in sequence with equal phase displacement intervals therebetween of 360° divided by the number of piston-cylinder units, said circular eccentric drive cam affording a non-linear relationship between the rotary speed of said motor and the linear speed of each piston-cylinder unit during its pumping stroke, a pressure transducer for producing an electrical signal corresponding to the pressure in said common discharge outlet, said piston-cylinder units producing a combined liquid discharge tending to have pressure pulsations therein at said common liquid discharge outlet, and an electronic control system connected between said pressure transducer and said stepping motor for regulating the instantaneous speed of said motor to maintain at least approximately constant outlet discharge pressure and thereby to maintain at least approximately constant discharge capacity, said electronic control system having fast response regulating means for rapidly changing the speed of said motor in response to outlet pressure pulsations during each cycle of said circular eccentric drive cam so as to minimize said pulsations and thereby compensate for the non-linear character of said drive cam so as to maintain the outlet pressure at least approximately constant during each cycle of said drive cam, said fast response regulating means including a high-pass filter for receiving and passing the pulsations in the pressure signals from said pressure transducer while withholding any substantial transmission of long term changes in the pressure signals, means for supplying a reference direct voltage, a summing stage for receiving the pulsating signals from said high-pass filter and for superimposing said pulsating signals upon said reference direct voltage to produce combined output signals, a threshhold value discriminator connected to said summing stage for receiving said combined output signals, an electronic driver connected to said stepping motor, pulse generating means connected to said driver of said stepping motor for producing motor control pulses to operate said stepping motor at a speed corresponding to the frequency of said pulses, said pulse generating means including switchable pulse frequency changing means for switching the motor control pulse frequency between a higher value and a lower value, electronic switching means connected between said threshhold value discriminator and said switchable means for switching the motor control pulse frequency between its two values to speed up and slow down the instantaneous speed of said stepping motor to minimize such output pressure pulsations, said pulse generating means comprising a pulse source for supplying source pulses of a frequency f, said switchable means of said pulse generating means comprising a switchable frequency divider having its input connected to said pulse source and switchable between two different division ratios for producing said higher and said lower frequency output pulses to change the speed of said stepping motor, said switchable frequency divider being switchable between division ratios of 1:1 and 1:2, and speed regulating means comprising first means for deriving first frequency pulses from said pulse source pulses and related in frequency to a mean speed to be established for the motor, second means for deriving second frequency pulses of a second frequency comparable with said first frequency as a function of the frequency of the output motor control pulses from said switchable frequency divider, difference means for deriving the difference between said first and second frequencies, and third means for producing a control voltage as a function of said difference and for employing said control voltage to vary said reference direct voltage in a direction to cause a reduction of said frequency difference, whereby the average frequency of said motor control pulses is regulated to correspond with said mean frequency, said electronic control system comprising compressibility compensating means for determining the compressibility of the liquid being pumped by the piston-cylinder units and for increasing the source pulse frequency f of the pulses from said pulse source as a function of such compressibility for correspondingly increasing the speed of the stepping motor and thereby compensating for such compressibility.

15. A multiple piston pump according to claim 14, said compressibility compensating means comprising a speed monitoring device for producing digital speed indicating pulses corresponding to the speed of said cam, instantaneous pressure transducers for producing instantaneous pressure signals corresponding to the instantaneous liquid pressures produced in said piston-cylinder units, and means for determining the compressibility of the liquid as a function of said digital speed indicating pulses and said instantaneous pressure signals and for correspondingly increasing the source pulse frequency f.

16. A multiple piston pump according to claim 14, said compressibility compensating means including a speed monitoring device for producing digital speed indicating pulses corresponding to the speed of said cam, instantaneous pressure transducers for producing instantaneous pressure signals corresponding to the instaneous pressures in said piston-cylinder units, and a microprocessor for determining the compressibility of the liquid as a function of said digital speed indicating pulses and said instantaneous pressure signals and for correspondingly increasing the source pulse frequency f.

17. A multiple piston pump according to claim 16, said pulse source comprising a fixed frequency oscillator for producing fixed frequency pulses, and a variable ratio frequency divider controllable by said microprocessor for variably dividing said fixed frequency to produce the source pulses of the frequency f which is increased as a function of the compressibility of the liquid.

18. A multiple piston pump according to claim 14, said difference means comprising an up-down counter having up and down counting inputs, said first means having its output connected to one of said counting inputs, said second means having its output connected to the other of said counting inputs, said up-down counter producing a digital count output corresponding to the difference between said first and second frequency, said third means comprising a digital to analog convertor for producing a control voltage corresponding to said digital count output, the output of said digital to analog convertor being connected to said summing stage to employ said control voltage to vary said reference direct voltage in such a direction as to reduce the difference between said first and second frequencies.

19. A multiple piston pump according to claim 18, said first means comprising a frequency divider having a division ratio of 1:3 to produce a first frequency which is one-third of the source pulse frequency f, said switchable frequency divider being switchable between division ratios of 1:1 and 1:2 and being capable of maintaining a mean output pulse frequency which is two-thirds of the source pulse frequency f, said switchable frequency divider being operative to suppress alternate pulses when switched to a division ratio of 1:2, said second means being operative to receive and utilize the suppressed pulses from said switchable frequency divider whereby said suppressed pulses are supplied as said second frequency pulses to be stabilized at an average frequency which is one-third of the source pulse frequency f.

* * * * *